United States Patent [19]

Fukuda

[11] Patent Number: 4,905,666
[45] Date of Patent: Mar. 6, 1990

[54] BENDING DEVICE FOR AN ENDOSCOPE
[75] Inventor: Hiroyuki Fukuda, Hachioji, Japan
[73] Assignee: Olympus Optical Co., Ltd., Japan
[21] Appl. No.: 337,287
[22] Filed: Apr. 13, 1989

Related U.S. Application Data

[62] Division of Ser. No. 168,264, Mar. 15, 1988, Pat. No. 4,841,950.

[30] Foreign Application Priority Data

Mar. 27, 1987 [JP] Japan .................................. 62-71641
Jul. 3, 1987 [JP] Japan .................................. 62-166669

[51] Int. Cl.⁴ .............................................. A61B 1/00
[52] U.S. Cl. ......................................................... 128/4
[58] Field of Search .......................................... 128/4, 6

[56] References Cited

U.S. PATENT DOCUMENTS 3,091,235 5/1963 Richards .................................. 128/6
3,610,231 10/1971 Takahashi ................................ 128/6
4,203,430 5/1980 Takahashi ................................ 128/4
4,294,233 10/1981 Takahashi ................................ 128/4

FOREIGN PATENT DOCUMENTS 59-31202 9/1984 Japan .
59-196207 12/1984 Japan .

Primary Examiner—William H. Grieb
Attorney, Agent, or Firm—Ostrolenk, Faber, Gerb & Soffen

[57] ABSTRACT

A bending device for an endoscope operates the bendable portion on the front end side of the insertable portion of the endoscope to bend by moving back and forth an operating wire which is inserted in a coil sheath housed within the insertable portion to connect the bendable portion and an operation portion for bending on the rear end side of the endoscope. The bending device prevents a relative looseness between the coil sheath and the operating wire by fixing the coil sheath at its end on the bendable portion side so as not to rotate around its axis and controlling rotation of the coil sheath at the other end on the operating portion side around the axis thereof within a limit.

6 Claims, 5 Drawing Sheets

BENDING DEVICE FOR AN ENDOSCOPE

This is a divisional of application Ser. No. 168,264, filed Mar. 15, 1988 now U.S. Pat. No. 4,841,950, issued on June 27, 1989.

BACKGROUND OF THE INVENTION

The present invention relates to a bending device for an endoscope which provides a bending operation for a bendable portion of the endoscope by moving back and forth an operating wire.

In general, medical endoscopes for observing and treating a coelom such as the stomach and intestines and industrial endoscopes for observing the inside of a tube such as used in a boiler and a chemical plant require to have a bendable function to direct the distal end of the insertable portion thereof to a desired direction.

To this end, such endoscope is provided with a bending device in which a guide sheath for operating wires comprising a pair of coil sheaths which are flexible but do not lengthen or shorten in theaxial direction is inserted into the insertable portion of the endoscope and operating wires are respectively inserted into the pair of coil sheaths so as to provide the bending operation to the bendable portion of the endoscope by moving back and forth the operating wires. Specifically, the coil sheath, which generally employs a closely wound coil, has a structure in which one end of the operating wire inserted in the closely wound coil is fixed to the distal end of the bendable portion and the other end thereof is connected to a bending operation portion which is provided in the operation portion of the endoscope so that the bending operation can be performed by moving back and forth the operating wires at the bending operation portion. With this structure, however, looseness would be caused between the coil sheath and the operating wire during the bending operation, which is caused by shrinkage of a bendable tube of the bendable portion and the coil sheath and elongation of the operating wire and the like.

In the case where the bending operation is performed by pulling the strained operating wire as described above, a compressive force is applied to a closely wound coil which forms the coil sheath.

The compressive force is twisted in a direction in which the closely wound coil is running down to act so as to axially shorten its length. Accordingly, when the bending operation is repeated, the closely coiled winding is reduced in length in its axial direction to cause looseness in the operating wire.

Such looseness involves a play which causes a phenomenon in which no bending is operated until the looseness is canceled, even when an operating lever or the like is moved, and reduction in a bending angle by a value initially being loosened to lower the insertability and the performance of observation and treatment of the endoscope.

A technique of canceling looseness is proposed, for example, in Japanese Utility Model Publication Sho59-31202.

In the proposed technique, a screw member is interposed in a part of an operating wire so as to change threadably engaging position of the screw member, thereby a distance between connecting portions of the screw member being changed by the screwing operation to adjust a length of the operating wire to cancel looseness.

In such technique, however, repairs and adjustments should be made whenever looseness is caused. Such correcting operation has to be conducted by a specialist, so that it interrupts the use of an endoscope and also is very expensive.

SUMMARY OF THE INVENTION

It is an object of the present invention to provide a bending device for an endoscope to reliably remove at least shrinkage of a coil sheath, which is one of the causes such as shrinkage of a bendable tube which forms the bendable portion and a coil sheath which forms a guide sheath and elongation of an operating wire for a relative looseness between the coil sheath and the operating wire in use for a long time.

According to the present invention, a bending device for an endoscope has no relative looseness between the coil sheath and the operating wire due to shrinkage of the coil sheath because the end portion of the coil sheath on the bendable portion side is fixed so as not to rotate around its axis and the other end portion thereof on the operation portion side is controlled in rotation around its axis with a limit (including a fixed condition).

BRIEF DESCRIPTION OF THE DRAWINGS

FIG. 11 being an exploded perspective view showing essential parts thereof and FIG. 12 being an explanatory view showing movement of the essential parts.

DETAILED DESCRIPTION OF PREFERRED EMBODIMENTS

Figure 1:
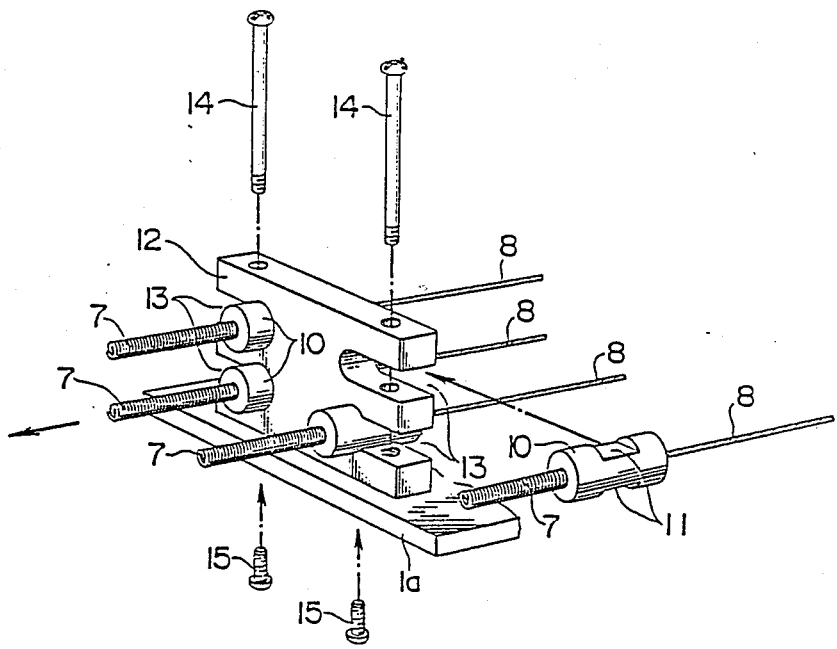
FIG. 1 and 2 show a first embodiment of a bending device for an endoscope according to the present invention, FIG. 1 being an exploded perspective view showing a fixing structure of a guide sheath on an operation portion side which is an essential part of the bending device and FIG. 2 being a schematic side view showing the bending device having the fixing structure shown in FIG. 1 together with an endoscope.
Figure 2:
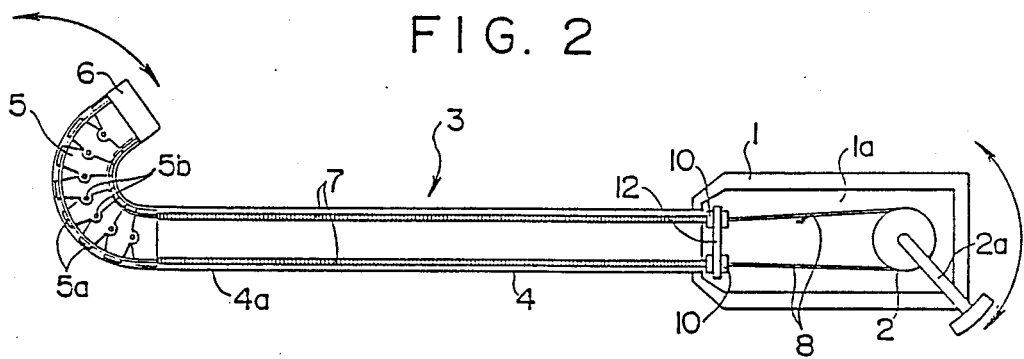

FIGS. 1 and 2 show a first embodiment of a bending device according to the present invention. Particularly, FIG. 2 schematically shows an endoscope such as a fiberscope and an electronic scope on the whole together with a bending device of the present invention. An operation portion 1 includes a pair of pulleys 2 (only one is shown in FIG. 2). A pair of operating levers 2a are respectively connected to the pair of pulleys 2, which constitute a bending operation portion together with the pulleys 2 so as to rotate the pulleys 2 around their center axis by rotating the operating levers 2a (only one is shown in FIG. 2).

On the other hand, an insertable portion 3 is formed, as is well known, by serially connecting a bendable portion 5 which is formed by rotatably connecting a plurality of articulated tube 5a arranged in series relationship one by one with rivets 5b and a distal end body 6 to a flexible tube 4. The insertable portion 3 is connected to the operation portion 1 to form an endoscope body.

A guide sheath 7 which guides operating wires 8 is formed by two pairs of closely wound coils (only a pair of coils are shown in FIG. 2) which are symmetrically inserted in the flexible tube 4 towards the inner wall thereof and into which the operating wires are respectively inserted.

The operating wires 8 which are wound on the respective pulleys 2 have their distal ends fixed to the distal end body 6 after being slidably inserted into the respective closely wound coils, so that the bendable portion 5 can be longitudinally and transversely bent by pulling the operating wires 8 with the operating lever 2a rotating. The portion of the operating wire which is wound on the pulley 2 is secured to the pulley 2.

The present invention is applied to the fixation of the rear (proximal) ends of the coil sheaths 7 of the structure just described above.

The opposite ends of the coil sheath 7 comprising a closely wound coil are fixed as follows. The front (distal) end of the coil sheath 7 on the bendable portion 5 side is fixed to the inner periphery of a mouthpiece 4a at the rear end of the bendable portion by brazing so that the front end of the coil sheath 7 can not rotate in a twisting direction. The fixation not to rotate around the axis of the coil sheath 7 may be carried out by soldering, adhesion or the like other than brazing.

The rear end of the coil sheath 7 on the operation portion 1 side is fixed, as shown in FIG. 1 in detail, to a stationary base plate 1a which constitutes the operation portion 1 with a fixing member.

Namely, as a fixing member a coil lock member 10 is employed which is in a substantially cylindrical form and has a through-hole of a diameter nearly equal to that of a closely wound coil of the coil sheath 7 on the central axis thereof. The coil lock member 10 is fixed to the rear end of each of the coil sheaths 7 on the operation portion 1 ide as by brazing.

A plurality of the operating wires 8 are inserted through the through-hole of the coil lock member 10. In addition, a pair of cut portions 11 are provided in the middle of the outer periphery of the coil lock member 10 so as to have respective planes in parallel to each other at symmetrical positions shifted by 180° each other.

A coil lock holder 12 is provided uprightly on the base plate 1a on the flexible tube 4 side so as to substantially perpendicularly cross with the direction of inserting the operating wires 8 through the coil sheaths 7 and is fixed to the base plate 1a with set screws 15. The holder 12 is made of a plate of the substantially same thickness as a width of the cut portion of the coil lock member 10. In addition, the holder 12 is provided with upper and lower slits 13 parallel to the plane of the base plate 1a on the transversely opposite sides of the base plate 1a and extending sideward from the position of the base plate 1a where the operating wire 8 is inserted. A width of the slits 13 is defined to the substantially same as a width between both cut portions 11, 11 so that the cut portions 11, 11 of the coil lock member 12 can be inserted into the slits 13 as shown in FIG. 1, resulting in that the slits 13 and the cut portions 11 are engaged together. Thereby, it is possible to fix the coil lock member 12 so as not to move and rotate it. In addition, a screw 14 for preventing the coil lock member 10 from escaping sideward is inserted on the transversely opposite sides of the holder 12 such that it passes through the holder 12 on the opening sides of the upper and lower slits 13, 13 so as not to slip off from the holder 12.

With the first embodiment of the above structure, when the operating lever 2a is rotated the operating wires 8 are moved back and forth through the pulleys 2 to bend the bendable portion 5 transversely and/or longitudinally.

When such bending operation is repeated, a compressive force caused in the coil sheath 7 works as an action of rotating in a direction of running down the closely wound coiled of the coil sheath 7 to unwind it, so that an axial length of the coil sheath 7 may be reduced because of reduction in the total number of pitches. In the first embodiment, however, since the front and rear ends of the operating wire 8 are respectively fixed by brazing and the engagement between the coil lock member 10 and coil lock holder 12, there is no rotation of the coil sheath 7 around its axis during the bending operation.

Accordingly, no relative distortion involves between the coil end portions on the bendable and operating portion sides, so that the total length of the coil sheath 7 is not reduced due to reduction of the total number of pitches as seen in the prior art device. As a result, even when an endoscope is used for a prolonged time, no relative losseness due to shrinkage of the coil sheath is caused between the coil sheath 7 and the operating wire 8.

Consequently, a play and reduction in a bending angle which are the causes for losseness are practically insignificant, so that it is possible to maintain good insertability and performance of observation and treatment of an endoscope for a prolonged time.

In addition, since there is no looseness, there is no possibility that the use of an endoscope is interrupted and the cost of repairing is reduced.

Other embodiments of the present invention will be described hereinafter with reference to FIGS. 3 to 12, wherein like reference characters designate like or corresponding parts throughout and their description will be omitted.

Figure 3:
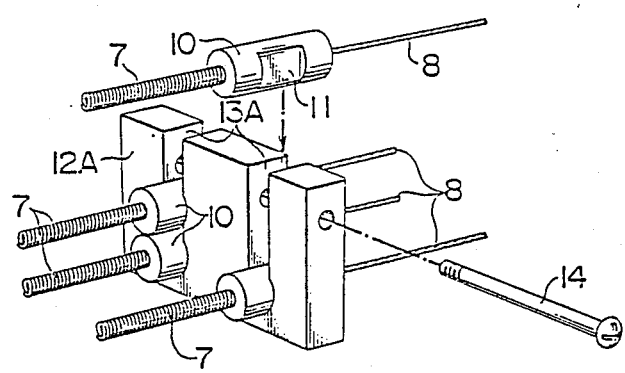
FIG. 3 is an exploded perspective view showing a second embodiment of a bending device for an endoscope according to the present invention.

In FIG. 3, which shows a second embodiment of the present invention, two vertical slits 13A are provided on a coil lock holder 12A so that two coil lock members 10 are inserted into the respective slits 13A.

The structure just described above has advantages that the coil lock holder 12A can be easily manufactured since the number of slits 13A is reduced and also the number of the screws 14 for preventing the coil lock member 10 from escaping can be reduced.

Figure 4:
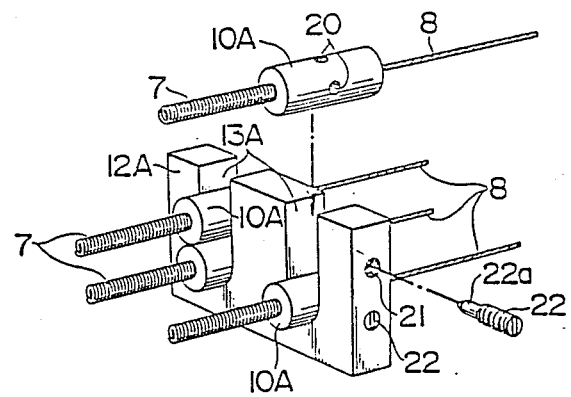
FIG. 4 is an exploded perspective view showing essential parts of a third embodiment of a bending device for an endoscope according to the present invention.

In FIG. 4, which shows a third embodiment of the present invention which is an example of modification of the second embodiment, a coil lock member 10A is fixed so as not to rotate around its axis by using screws.

Specifically, a plurality of cone shaped holes 20 are circumferentially provided on the middle of the outer periphery of the cylindrical coil lock member 10A and screw holes 21 are provided on the transversely outer sides of the coil lock holder 12A at positions corresponding to the respective holes 20 of the coil lock members 10A inserted in the slits 13A in place. With such structure, after the coil lock member 10A is inserted in the slit 13A in place, a set screw 22 is screwed through the screw hole 21 to press a conical end 22a of the screw 22 against the hole 20, thereby the coil lock member 10A being fixed.

Figure 5:
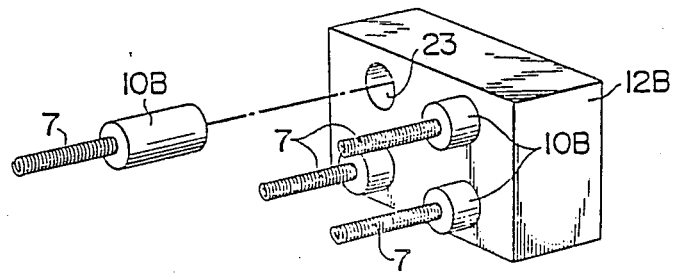
FIG. 5 is an exploded perspective view showing essential parts of a fourth embodiment of a bending device for an endoscope according to the present invention.

In FIG. 5, which shows a fourth embodiment of the present invention, through-holes 23 having a diameter substantially equal to that of a cylindrical coil lock member 10B are provided on a coil lock holder 12B. The coil lock member 10B is inserted into the through-hole 23 to fix it by brazing, soldering or adhesion so that the coil lock member 10B does not rotate around its axis.

With the structure described above, since the coil lock holder 12B will do as long as only the through-hole 23 is provided thereon and the coil lock member 10B will do for use in a cylindrical form and need not to provide any working, both members can be easily manufactured.

In addition, since the coil lock member 10B can be fixed any position around its axis to the coil lock holder 12B, it is easily assembled.

Figure 6:
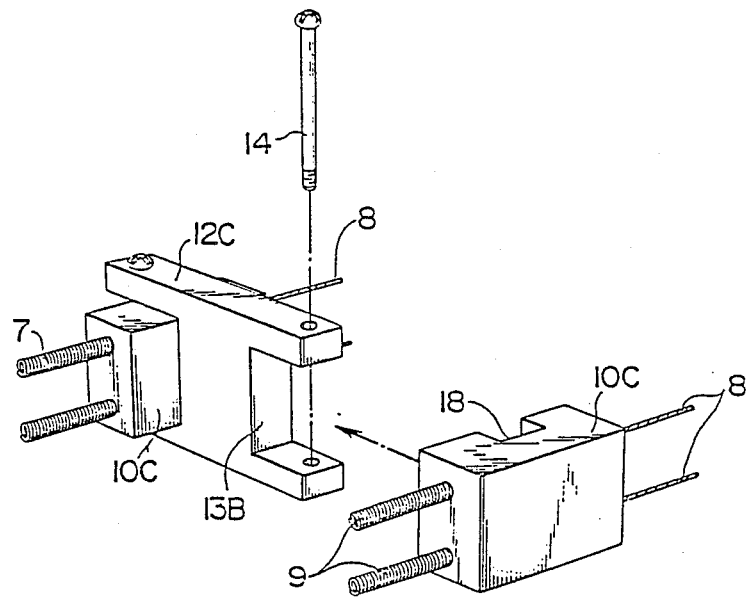
FIG. 6 is an exploded perspective view showing essential parts of a fifth embodiment of a bending device for an endoscope according to the present invention.

In FIG. 6, which shows a fifth embodiment of the present invention, a coil lock member 10C which is formed in a substantially rectangular parallelepiped has two through-holes 9 of a diameter nearly equal to that of a closely wound coil of the coil sheath 7 and grooves 18 on the inner side thereof which fit in horizontal slits 13B provided on the opposite sides of a coil lock holder 12C.

The coil lock member 10C is fixed, after the groove 18 is fit in the slit 13B, to the coil lock holder 12C by a screw 14. With this structure, it is also possible to fix the coil sheath 7 so as not to rotate around its axis.

Figure 7:
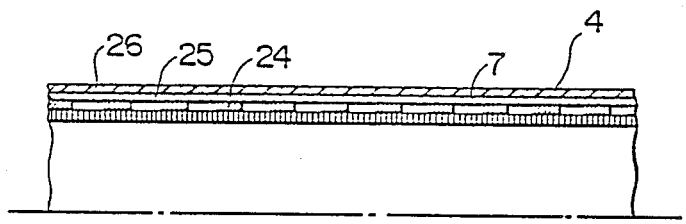
FIG. 7 is a section view showing essential parts of a sixth embodiment of a bending device for an endoscope according to the present invention.

In FIG. 7, which shows a sixth embodiment of the present invention, the coil sheath 7 comprising a closely wound coil is fixed to the inner periphery of the insertable portion 3, that is, the inner periphery of a flex 24 comprising a helical tube of the flexible tube 4 which comprises the flex 24, a blade 25 comprising a netted tube and a housing 26, at a plurality of positions of a given interval over the substantially overall length of the closely wound coil by brazing, soldering, adhesion or the like.

Figure 8:
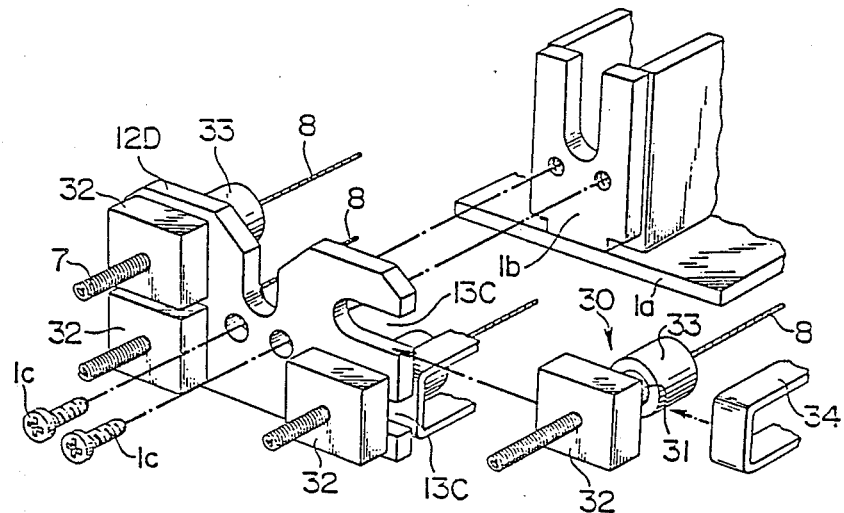
FIGS. 8 to 10 show a seventh embodiment of a bending device for an endoscope according to the present invention, FIG. 8 being an exploded perspective view showing essential parts thereof, FIG. 9 being an enlarged front view showing essential parts thereof and FIG. 10 being an explanatory view showing movement of the essential parts.
Figure 9:
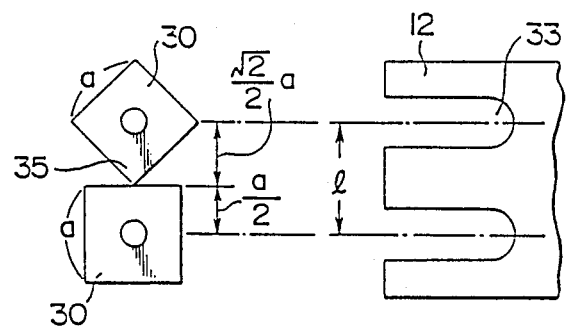
Figure 10:
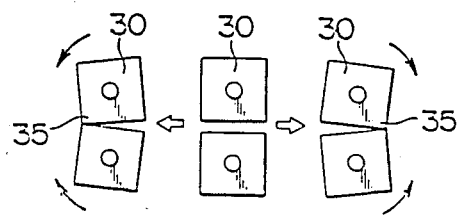

In FIG. 8 to 10, which shows a seventh embodiment of the present invention, a coil lock member 30 has a through-hole of a diameter nearly equal to that of a closely wound coil forming the coil sheath 7 on the central axis thereof, and is formed of a large diameter portion 33 at the rear end thereof, a small diameter portion 31 in the middle thereof and a substantially rectangular parallelpiped portion 32 at the front end thereof. The coil lock member 30 is fixed at the rear end of the coil sheath 7 on the operation portion 1 side as by soldering. The operating wire 8 is inserted into and fixed to the inside of the coil lock member 30. A coil lock holder 12D is provided with upper and lower slits 13C formed in parallel with the base plate 1a of the operation portion 1 on the transversely opposite sides thereof. The small diameter portion 31 is rotatably inserted in the slit 13C. The coil lock holder 12D is fixed by a screw 1c at the center portion thereof to a holder fixing member 1b which has a plane perpendicular to the base plate 1a and is fixed to the latter. In addition, a member 34 is fixed to the coil lock holder 12D in abutment with the coil lock member 30 front the opening side of the slits 13C such that the coil lock member 30 does not slip off on the slit 13C. In this embodiment, the portion 32 of the coil lock member 30 forms an anti-rotation portion 35 in the side corner thereof, as shown in FIG. 9. When the portion 32 whose section perpendicular to the axis thereof is square, for example, a side length a of the square is taken to meet the following, $$\frac{1+\sqrt{2}}{2} a > l$$

where l represents a distance between the center axes of slits 13C.

With the structure described above, even when the closely wound coil of the coil sheath 7 is going to rotate in a direction of its running down, the anti-rotation portion 35 strikes against another coil lock member 30, as shown in FIG. 10, so that the rotation can be controlled within a given value. In this case, the maximum rotation angle is less than 90°.

Namely, there is little relative distortion between coils on the bendable portion 5 and operation portion 1 sides, so that there is no possibility that the overall length of the coil sheath 7 is so reduced due to reduction of the total number of pitches that it exerts a great influence on a play and reduction in a bending angle as seen in the past.

Figure 11:
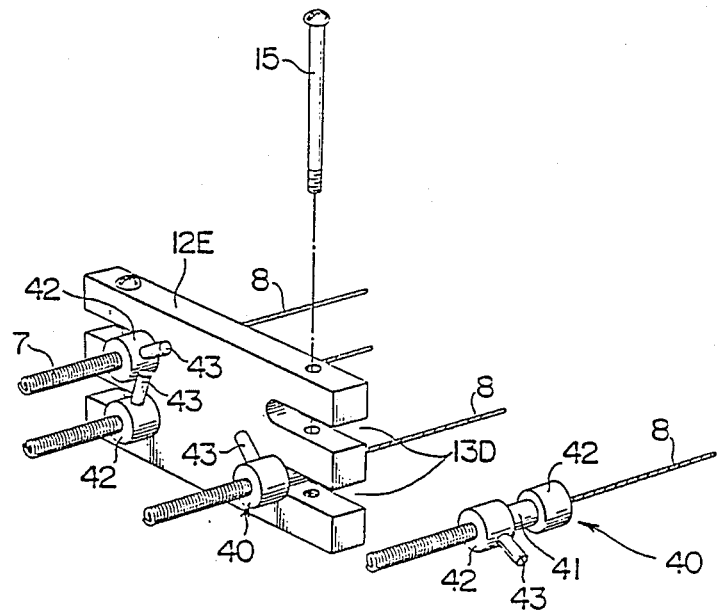
FIGS. 11 and 12 show an eighth embodiment of a bending device for an endoscope according to the present invention.
Figure 12:
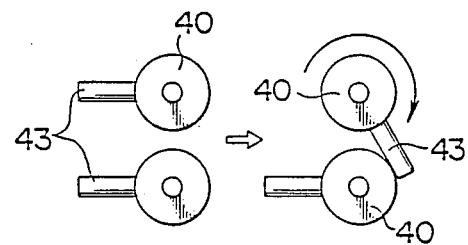

In FIGS. 11 and 12, which show an eighth embodiment of the present invention, a coil lock member 40 is in a substantially cylindrical form and has a small diameter portion 41 and large diameter portions 42 at opposite ends thereof. An anti-rotation pin 43 radially extends from the periphery of the large diameter portion 42. The small diameter portion 41 is rotatably inserted in a slit 13D of a coil lock holder 12E.

With this structure, the rotation of the closely wound coil of the coil sheath 7 can be controlled within a limited value by the anti-rotation pin 43 since, as shown in FIG. 12, the pin 43 is brought into contact with another coil lock member 40 so as not to rotate any more.

According to the present invention, as described above, it is possible to control the rotation of the guide sheath around its axis which is a cause of the looseness within a limit, so that no relative looseness between the guide sheath and operating wire due to shrinkage of the coil sheath can be caused.

As a result, a play and reduction of a bending angle are practically insignificant and it is possible to retain a good insertability and performance of observation and treatment of an endoscope for a prolonged time. In addition, because of no looseness, the use of an endoscope is not interrupted and the expense for repairing is not increased.

Experimental results confirming the effects described above are shown as follows.

With an endoscope for the colon, a life tolerance test is conducted to the guide sheaths controlled and not controlled in rotation around its axis to measure a play and reduction of a bending angle.

TABLE 1

|  | Reduction of a bending angle | Play |
|---|---|---|
| One controlled in rotation | 25° | 50° |
| One not controlled in rotation | 45° | 75° |

As shown in Table 1, a play and reduction of a bending angle can be so reduced by controlling the rotation of the guide sheath that there is practically no problem.

What is claimed is:

1. A bending device for an endoscope including:
a coil sheath housed within the insertable portion thereof and an operating wire inserted in said coil sheath for connecting a bendable portion on the distal end side of said insertable portion and a bending operating portion on the proximal end side of the endoscope, characterized by:
fixing means for fixing the distal end of said coil sheath on the bendable portion side so as not to rotate around its axis; and
a coil lock member secured to the proximal end of the coil sheath at the operating side; and
a coil lock holder disposed at the operating side and having an engagement portion which engages with said coil lock member to prevent the coil lock member from rotating around its axis.

2. A bending device according to claim 1 in which:
said coil lock member is in a insubstantially cylindrical form with a pair of cut portions provided in the middle of the outer periphery thereof so as to have respective planes in parallel to each other at symmetrical positions shifted by 180°, in which the proximal end of the coil sheath is fixed after being inserted on the center axis of the coil lock member, said coil lock holder being formed by a plate member and being provided with a horizontal slit for receiving said cut portion, thereby preventing said coil sheath from rotating by fitting said coil lock member in said coil lock holder.

3. A bending device according to claim 1 in which:
said coil lock member is in a substantially cylindrical form with a pair of cut portions provided in the middle of the outer periphery thereof so as to have respective planes in parallel to each other at symmetrical positions shifted by 180°, in which the proximal end of the coil sheath is fixed after being inserted on the center axis of the coil lock member, said coil lock holder being formed by a plate member and being provided with a vertical slit for receiving said cut portion, thereby preventing said coil sheath from rotating by fitting said coil lock member in said coil lock holder.

4. A bending device according to claim 1 in which:
said coil lock member is in a substantially cylindrical form with a hole provided in the middle of the outer periphery thereof, in which the proximal end of the coil sheath is fixed after being inserted on the center axis of the coil lock member, said coil lock holder being formed by a plate member in which a slit is provided for inserting said coil lock member therein,
thereby preventing said coil sheath from rotating by inserting a set screw passing through said coil lock member in said hole after said coil lock member is fitted in said coil lock holder.

5. A bending device according to claim 1 in which:
said coil lock member is in a substantially rectangular parallelepiped form provided with a groove on the one vertical side thereof and said coil lock holder being formed by a plate member provided with a horizontal slit, thereby preventing said coil sheath from rotating by inserting said coil lock member in said horizontal slit so as to engagingly fit said groove with said horizontal slit.

6. A bending device according to claim 1 in which said coil lock member into which said coil sheath is inserted and secured thereto is inserted into said coil lock holder and is fixed thereto by an adhesion process for preventing said coil sheath from rotating.

* * * * *